US010224486B2

(12) United States Patent
Yagi et al.

(10) Patent No.: US 10,224,486 B2
(45) Date of Patent: Mar. 5, 2019

(54) COMPOUND FOR ORGANIC PHOTOELECTRIC DEVICE AND ORGANIC PHOTOELECTRIC DEVICE AND IMAGE SENSOR INCLUDING THE SAME

(71) Applicant: Samsung Electronics Co., Ltd., Suwon-si, Gyeonggi-do (KR)

(72) Inventors: Tadao Yagi, Hwaseong-si (KR); Rie Sakurai, Suwon-si (KR); Hyesung Choi, Seoul (KR); Tatsuya Imase, Yokohama (JP); Hiromasa Shibuya, Seongnam-si (KR); Sung Young Yun, Suwon-si (KR); Gae Hwang Lee, Seongnam-si (KR); Kwang Hee Lee, Yongin-si (KR); Dong-Seok Leem, Hwaseong-si (KR); Seon-Jeong Lim, Yongin-si (KR); Xavier Bulliard, Seongnam-si (KR); Yong Wan Jin, Seoul (KR); Yeong Suk Choi, Suwon-si (KR); Moon Gyu Han, Suwon-si (KR)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 0 days.

(21) Appl. No.: 15/272,580

(22) Filed: Sep. 22, 2016

(65) Prior Publication Data

US 2017/0092868 A1    Mar. 30, 2017

(30) Foreign Application Priority Data

Sep. 25, 2015    (KR) .................... 10-2015-0136924

(51) Int. Cl.
*H01L 51/00*    (2006.01)
*H01L 51/42*    (2006.01)
*H01L 27/30*    (2006.01)
*C07D 333/36*    (2006.01)
*C07D 345/00*    (2006.01)

(52) U.S. Cl.
CPC ........ *H01L 51/0061* (2013.01); *C07D 333/36* (2013.01); *C07D 345/00* (2013.01); *H01L 51/006* (2013.01); *H01L 51/0052* (2013.01); *H01L 51/0054* (2013.01); *H01L 51/0062* (2013.01); *H01L 51/0068* (2013.01); *H01L 27/307* (2013.01); *H01L 51/0046* (2013.01); *H01L 51/4253* (2013.01); *Y02E 10/549* (2013.01)

(58) Field of Classification Search
CPC ............ H01L 51/0061; H01L 51/0054; H01L 51/0052; H01L 51/0068; H01L 51/0062; H01L 51/006; H01L 51/4253; H01L 51/0046; H01L 27/307; C07D 333/36; C07D 345/00; Y02E 10/549
See application file for complete search history.

(56) References Cited

U.S. PATENT DOCUMENTS

| 6,087,258 A | 7/2000 | Simpson et al. |
| 6,300,612 B1 | 10/2001 | Yu |
| 6,824,952 B1 | 11/2004 | Minsek et al. |
| 6,972,431 B2 | 12/2005 | Forrest et al. |
| 7,129,466 B2 | 10/2006 | Iwasaki |
| 7,141,863 B1 | 11/2006 | Compaan et al. |
| 7,973,307 B2 | 7/2011 | Rand et al. |
| 8,035,708 B2 | 10/2011 | Takizawa et al. |
| 8,378,339 B2 | 2/2013 | Nomura et al. |
| 8,426,727 B2 | 4/2013 | Pfeiffer et al. |
| 8,471,246 B2 | 6/2013 | Suzuki et al. |
| 8,525,577 B2 | 9/2013 | Yofu et al. |
| 8,637,860 B2 | 1/2014 | Nomura et al. |
| 8,704,213 B2 | 4/2014 | Suzuki |
| 8,704,281 B2 | 4/2014 | Maehara et al. |
| 8,847,141 B2 | 9/2014 | Fukuzaki et al. |
| 8,847,208 B2 | 9/2014 | Mitsui et al. |
| 8,860,016 B2 | 10/2014 | Suzuki |
| 8,933,438 B2 | 1/2015 | Leem et al. |
| 8,994,132 B2 | 3/2015 | Mitsui et al. |
| 9,070,888 B2 | 6/2015 | Leem |
| 9,543,361 B2 | 1/2017 | Leem et al. |
| 9,548,463 B2 | 1/2017 | Yagi et al. |
| 9,960,362 B2 | 5/2018 | Bulliard et al. |
| 2005/0217722 A1 | 10/2005 | Komatsu et al. |
| 2007/0012955 A1 | 1/2007 | Ihama |
| 2007/0063156 A1 | 3/2007 | Hayashi |
| 2007/0090371 A1 | 4/2007 | Drechsel et al. |

(Continued)

FOREIGN PATENT DOCUMENTS

| CN | 104230953 A | 12/2014 |
| DE | 102004014046 A1 | 9/2004 |

(Continued)

OTHER PUBLICATIONS

Hokuto Seo et al. "Color Sensors with Three Vertically Stacked Organic Photodetectors". Japanese Journal of Applied Physics vol. 46, No. 49. The Japan Society of Applied Physics. 2007. pp. L1240-L1242.

Satoshi Aihara et al. "Stacked Image Sensor With Green- and Red-Sensitive Organic Photoconductive Films Applying Zinc Oxide Thin-Film Transistors to a Signal Readout Circuit". IEEE Transactions on Electron Devices, vol. 56, No. 11. Nov. 2009. pp. 2570-2576.

Juha Alakarhu. "Image Sensors and Image Quality in Mobile Phones". International Image Sensor Workshop. 2007. pp. 1-4.

U.S. Appl. No. 15/461,914, filed Mar. 17, 2017.

(Continued)

*Primary Examiner* — John M Mauro
(74) *Attorney, Agent, or Firm* — Harness, Dickey & Pierce, P.L.C.

(57) ABSTRACT

A compound for an organic photoelectric device is represented by Chemical Formula 1. An organic photoelectric device includes a first electrode and a second electrode facing each other, and an active layer including the compound represented by Chemical Formula 1 between the first electrode and the second electrode.

23 Claims, 7 Drawing Sheets

(56) References Cited

U.S. PATENT DOCUMENTS

| | | |
|---|---|---|
| 2010/0207112 A1 | 8/2010 | Furst et al. |
| 2011/0012091 A1 | 1/2011 | Forrest et al. |
| 2011/0074491 A1 | 3/2011 | Yofu et al. |
| 2012/0126204 A1 | 5/2012 | So et al. |
| 2012/0266958 A1 | 10/2012 | Aksu et al. |
| 2012/0313088 A1 | 12/2012 | Yofu et al. |
| 2013/0087682 A1 | 4/2013 | Nomura |
| 2013/0181202 A1 | 7/2013 | Yofu et al. |
| 2014/0008619 A1 | 1/2014 | Lee et al. |
| 2014/0054442 A1 | 2/2014 | Huang et al. |
| 2014/0083496 A1 | 3/2014 | Shibasaki et al. |
| 2014/0159752 A1 | 6/2014 | Tsai et al. |
| 2014/0209173 A1 | 7/2014 | Momose |
| 2014/0319509 A1 | 10/2014 | Hattori et al. |
| 2015/0053942 A1 | 2/2015 | Kho et al. |
| 2015/0060775 A1 | 3/2015 | Liang et al. |
| 2015/0162548 A1 | 6/2015 | Lim et al. |
| 2015/0228811 A1 | 8/2015 | Hiroi et al. |
| 2015/0349073 A1 | 12/2015 | Kang |
| 2016/0013248 A1 | 1/2016 | Sawaki |
| 2016/0013424 A1 | 1/2016 | Yamamoto et al. |
| 2016/0020258 A1 | 1/2016 | Park et al. |
| 2016/0064672 A1 | 3/2016 | Lee et al. |
| 2016/0099417 A1 | 4/2016 | Sato et al. |
| 2016/0111561 A1 | 4/2016 | Hsu et al. |
| 2016/0111651 A1 | 4/2016 | Yun et al. |
| 2016/0126470 A1 | 5/2016 | Ro et al. |
| 2016/0149132 A1 | 5/2016 | Lim et al. |
| 2016/0197281 A1 | 7/2016 | Momose et al. |
| 2016/0268401 A1 | 9/2016 | Aleksov |
| 2017/0074652 A1 | 3/2017 | Send et al. |
| 2017/0117424 A1 | 4/2017 | Hiroi et al. |
| 2017/0294589 A1 | 10/2017 | Shibuya et al. |

FOREIGN PATENT DOCUMENTS

| | | |
|---|---|---|
| EP | 0529162 A1 | 3/1993 |
| EP | 2317582 A1 | 5/2011 |
| EP | 30267722 | 6/2016 |
| JP | H09-311232 A | 12/1997 |
| JP | H10-91384 A | 4/1998 |
| JP | 2005-132914 A | 5/2005 |
| JP | 2006-261172 A | 9/2006 |
| JP | 2007-234650 A | 9/2007 |
| JP | 2009-274966 A | 11/2009 |
| JP | 2011-225544 A | 11/2011 |
| JP | 2011-253861 A | 12/2011 |
| JP | 2012-123292 A | 6/2012 |
| JP | 2012-151761 A | 8/2012 |
| JP | 2013-040147 A | 2/2013 |
| JP | 5323025 B2 | 10/2013 |
| JP | 2014-049559 A | 3/2014 |
| JP | 2014-210768 A | 11/2014 |
| JP | 2015-015415 A | 1/2015 |
| JP | 2015-043362 A | 3/2015 |
| JP | 2015070060 A | 4/2015 |
| JP | 2015-092546 A | 5/2015 |
| KR | 10-2014-0106767 A | 9/2014 |
| KR | 10-2015-0066616 A | 6/2015 |
| KR | 10-2016-0009404 A | 1/2016 |
| KR | 10-2016-0024686 A | 3/2016 |
| KR | 10-2016-0052448 A | 5/2016 |
| KR | 10-2016-0062708 A | 6/2016 |
| WO | WO-2002-064600 A1 | 8/2002 |
| WO | WO-2008/091670 A2 | 7/2008 |
| WO | WO-2010/011658 A2 | 1/2010 |
| WO | WO-2010/038721 A1 | 4/2010 |
| WO | WO-2014-157238 A1 | 10/2014 |
| WO | WO-2014/169270 A2 | 10/2014 |

OTHER PUBLICATIONS

Drechsel J. et al: "Efficient organic solar cells based on a double p-i-n architecture using doped wide-gap transport layers", Applied Physics Letters, AIP Publishing LLC, US, vol. 86, No. 24, Jun. 7, 2005 (Jun. 7, 2005), pp. 244102-244102, XP012065900, ISSN: 0003-6951, DOI: 10.1063/1.1935771.

I.G. Hill et al., Organic Electronics, "Metal-dependent charge transfer and chemical interaction at interfaces between 3,4,9,10-perylenetetracarboxylic bisimidazole and gold, silver and magnesium", vol. 1, Issue 1, Dec. 2000, pp. 5-13.

Marzena Grucela-Zajac et al., "(Photo)physical Properties of New Molecular Glasses End-Capped with Thiophene Rings Composed of Diimide and Imine Units", The Journal of Physical Chemistry, May 21, 2014, pp. 13070-13086, ACS Author Choice.

Gorkem Memisoglu et al., "Highly Efficient Organic UV Photodetectors Based on Polyfluorene and Naphthalenediimide Blends: Effect of Thermal Annealing", 2012, International Journal of Photoenergy vol. 2012, Article ID 936075, 11 pages, Hindawi Publishing Corporation.

Jiri Misek et al., "A Chiral and Colorful Redox Switch: Enhanced p Acidity in Action", 2010, Angew. Chem. Int. Ed. 2010, 49, 7680-7683, Wiley-VCH Verlag GmbH & Co. KGaA, Weinheim.

Ihama, et al. "CMOS Image Sensor with a Thin Overlaid Panchromatic Organic Photoconductive Layer for Sensors with Reduced Pixel Size," IDW'09, pp. 2123-2126.

Iwaoka, et al. "Possible roles of S O and S N interations in the functions and evolution of phospholipase $A_2$," Biophysics, vol. 2, pp. 23-34 (2006).

Iwaoka, et al. Studies on the Nonbonded Interactions of Divalent Organic Selenium, Department of Chemistry, School of Science, Tokai University, vol. 63, No. 9, pp. 63-72 (2005).

Jen, et al. "Synthesis and Characterization of Highly Efficient and Thermally Stable Diphenylamino-Substituted Thiophene Stilbene Chromophores for Nonlinear Optical Applications," Advanced Materials, . vol. 9, No. 2, pp. 132-135 (1997).

Lim, et al. "Organic-on-silicon complementary metal-oxide-semiconductor colour image sensors," Scientific Reports, vol. 5, pp. 1-7 (2014).

Singh, et al. "Radical Cations of Aromatic Selenium Compounds: Role of Se X Nonbonding Interations," The Journal of Physical Chemistry, vol. 117, pp. 9259-9265 (2013).

European Search Report dated Apr. 26, 2017 issued in corresponding European Application No. 16195944.0.

European Search Report for Application No. 17177002.7 dated Nov. 17, 2017.

European Search Report issued in corresponding European Patent Application No. 17150423.6-1555 dated Aug. 4, 2017.

European Search Report dated May 22, 2017 issued in European Application No. 17161078.5.

U.S. Notice of Allowance dated Dec. 20, 2017 issued in copending U.S. Appl. No. 15/609,125.

U.S. Office Action dated Jan. 5, 2018 issued in copending U.S. Appl. No. 15/362,964.

U.S. Office Action dated Jun. 1, 2018 issued in copending U.S. Appl. No. 15/362,964.

U.S. Office Action dated Jul. 3, 2017 issued in copending U.S. Appl. No. 15/255,649.

U.S. Office Action dated Jan. 29, 2018 issued in copending U.S. Appl. No. 15/255,649.

COMPOUND FOR ORGANIC PHOTOELECTRIC DEVICE AND ORGANIC PHOTOELECTRIC DEVICE AND IMAGE SENSOR INCLUDING THE SAME

CROSS REFERENCE TO RELATED APPLICATION

This application claims priority to and the benefit of Korean Patent Application No. 10-2015-0136924 filed in the Korean Intellectual Property Office on Sep. 25, 2015, the entire contents of which are incorporated herein by reference.

BACKGROUND

1. Field

Example embodiments relate to a compound for an organic photoelectric device, and an organic photoelectric device and an image sensor including the same.

2. Description of the Related Art

A photoelectric device typically converts light into an electrical signal using photoelectric effects, and may include a photodiode, a phototransistor, etc. The photoelectric device may be applied to an image sensor, a solar cell, an organic light emitting diode, etc.

An image sensor including a photodiode requires typically high resolution, and thus, a relatively small pixel. At present, a silicon photodiode is widely used, but exhibits deteriorated sensitivity because of a relatively small absorption area due to the relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter, thereby improving sensitivity and contributing to relatively high integration.

SUMMARY

Example embodiments relate to a compound for an organic photoelectric device being capable of selectively absorbing light in a green wavelength region and having relatively high absorption intensity in a green wavelength region.

Example embodiments also relate to an organic photoelectric device being capable of selectively absorbing light in a green wavelength region and improving efficiency.

Example embodiments also relate to an image sensor including the organic photoelectric device.

Example embodiments also relate to an electronic device including the image sensor.

According to example embodiments, a compound for an organic photoelectric device is represented by Chemical Formula 1.

[Chemical Formula 1]

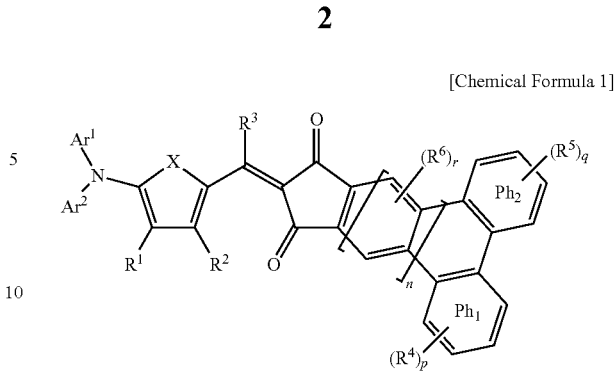

In Chemical Formula 1, each of $Ar^1$ and $Ar^2$ are independently one of a substituted or unsubstituted $C_6$ to $C_{30}$ aryl group and a substituted or unsubstituted $C_4$ to $C_{30}$ heteroaryl group, X is one of S, Se, Te, S(=O), S(=O)$_2$, and $SiR^aR^b$ (wherein each of $R^a$ and $R^b$ are independently one of hydrogen, a $C_1$ to $C_{10}$ alkyl group, a $C_6$ to $C_{10}$ aryl group, and a $C_5$ to $C_{10}$ heteroaryl group), each of $R^1$ to $R^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, and CN, each of p and q are independently integers of 0 to 4, r is an integer of 0 to 2, n is 0 or 1, and each of $Ph_1$ and $Ph_2$ are independently a fused phenylene ring, provided that at least one of $Ph_1$ and $Ph_2$ are present.

At least one of $Ar^1$ and $Ar^2$ may be one of a naphthyl group and an anthracenyl group.

The compound may have a maximum absorption wavelength ($\lambda_{max}$) at about 500 nm to about 600 nm, for example, about 530 nm to about 570 nm.

The compound may exhibit a light absorption curve having a full width at half maximum (FWHM) in a thin film state of about 50 nm to about 120 nm, for example, about 50 nm to about 110 nm.

The compound may be a p-type semiconductor compound.

According to example embodiments, an organic photoelectric device includes a first electrode and a second electrode facing each other, and an active layer between the first electrode and the second electrode, the active layer including the compound represented by Chemical Formula 1.

The active layer may have an absorption coefficient of greater than or equal to about $6 \times 10^4$ cm$^{-1}$, for example, about $6 \times 10^4$ cm$^{-1}$ to about $6.7 \times 10^4$ cm$^{-1}$, when including the compound and $C_{60}$ in a volume ratio of about 0.9:1 to about 1.1:1.

The active layer may have a maximum absorption wavelength ($\lambda_{max}$) of at about 500 nm to about 600 nm, for example, about 530 nm to about 570 nm.

The active layer may exhibit a light absorption curve having a full width at half maximum (FWHM) in a thin film state of about 50 nm to about 120 nm, for example, about 50 nm to about 110 nm.

The compound may be a p-type semiconductor compound.

The active layer may further include an n-type semiconductor compound, and the n-type semiconductor compound may include one of sub-phthalocyanine, fullerene or a fullerene derivative, thiophene or a thiophene derivative, and a combination thereof.

According to example embodiments, an image sensor includes the organic photoelectric device.

The image sensor may further include a semiconductor substrate integrated with a plurality of first photo-sensing devices configured to sense light in a blue wavelength region and a plurality of second photo-sensing devices configured to sense light in a red wavelength region. The organic photoelectric device may be on the semiconductor substrate and may be configured to selectively absorb light in a green wavelength region.

The plurality of first photo-sensing devices and the plurality of second photo-sensing devices may be stacked in a vertical direction on the semiconductor substrate.

The image sensor may further include a color filter layer between the semiconductor substrate and the organic photoelectric device, the color filter layer including a blue filter configured to selectively absorb light in a blue wavelength region and a red filter configured to selectively absorb light in a red wavelength region.

The organic photoelectric device may be a green photoelectric device, and the green photoelectric device, a blue photoelectric device configured to selectively absorb light in a blue wavelength region, and a red photoelectric device configured to selectively absorb light in a red wavelength region may be stacked.

According to example embodiments, an electronic device includes the image sensor.

DETAILED DESCRIPTION

Figure 1:
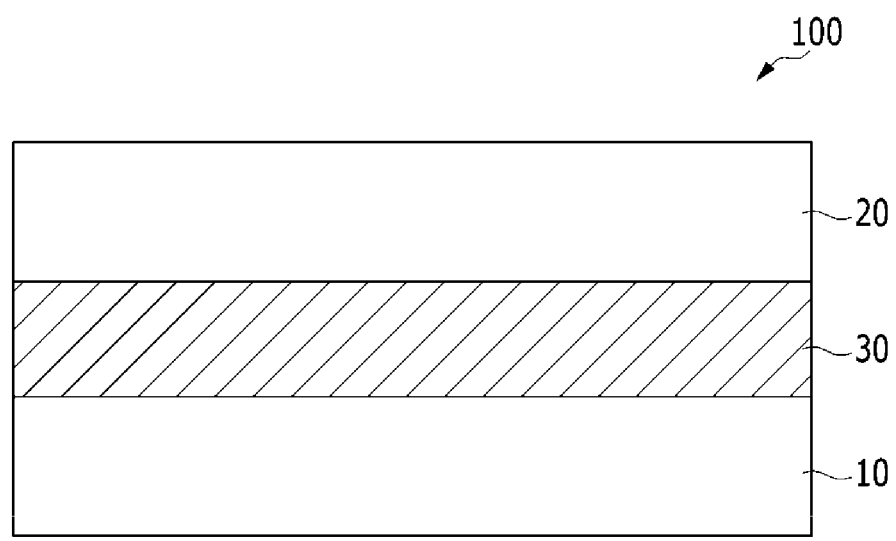
FIG. 1 is a cross-sectional view showing an organic photoelectric device according to example embodiments.

Example embodiments will hereinafter be described in detail, and may be easily performed by those who have common knowledge in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when specific definition is not otherwise provided, the term "substituted" refers to one substituted with a substituent selected from a halogen (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a $C_1$ to $C_{20}$ alkyl group, a $C_1$ to $C_{20}$ alkoxy group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{20}$ heteroalkyl group, a $C_1$ to $C_{20}$ heteroaryl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound or a functional group.

As used herein, when specific definition is not otherwise provided, the term "hetero" refers to one including 1 to 3 heteroatoms selected from N, O, S, P, and Si.

Hereinafter, a compound for an organic photoelectric device according to example embodiments is described.

A compound for an organic photoelectric device according to example embodiments is represented by Chemical Formula 1.

[Chemical Formula 1]

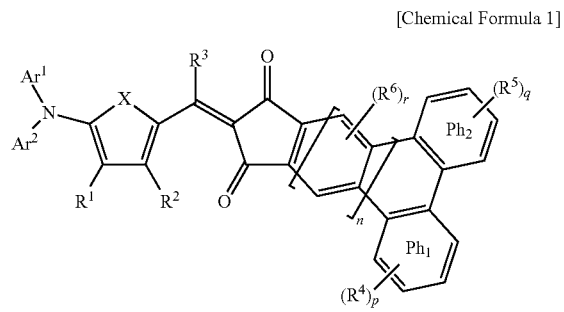

In Chemical Formula 1, each of $Ar^1$ and $Ar^2$ are independently one of a substituted or unsubstituted $C_6$ to $C_{30}$ aryl group and a substituted or unsubstituted $C_4$ to $C_{30}$ heteroaryl group, X is one of S, Se, Te, S(=O), S(=O)$_2$, and SiR$^a$R$^b$ (wherein each of R$^a$ and R$^b$ are independently one of hydrogen, a $C_1$ to $C_{10}$ alkyl group, a $C_6$ to $C_{10}$ aryl group, and a $C_5$ to $C_{10}$ heteroaryl group), each of $R^1$ to $R^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, and CN, each of p and q are independently integers of 0 to 4, r is an integer of 0 to 2, n is 0 or 1, and each of Ph$_1$ and Ph$_2$ are independently a fused phenylene ring, provided that at least one of Ph$_1$ and Ph$_2$ are present.

In Chemical Formula 1, the Ph$_1$ and Ph$_2$ are independently a phenylene ring fused with 1,3-indandione when n is 0 and a phenylene ring fused with benz[f]indene-1,3-dione when n is 1.

In Chemical Formula 1, a compound for an organic photoelectric device without one of the Ph$_1$ or Ph$_2$ may be represented by Chemical Formula 1A and 1B.

[Chemical Formula 1A]

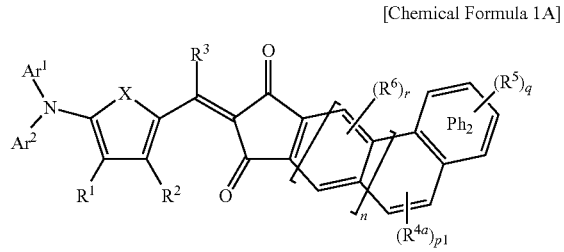

[Chemical Formula 1B]

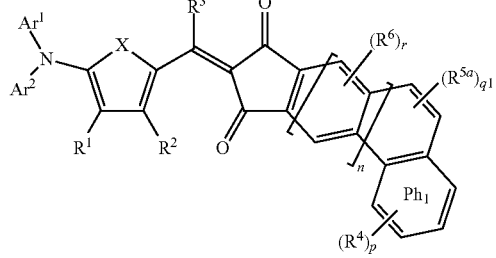

In Chemical Formulae 1A and 1B, $Ar^1$, $Ar^2$, X, and $R^1$ to $R^6$ are the same as in Chemical Formula 1, $R^{4a}$ and $R^{5a}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, and CN, and p1 and q1 are independently an integer of 0 to 2.

According to example embodiments, in the $Ar^1$, $Ar^2$, and $R^1$ to $R^6$, the term "substituted" refers to one substituted with, for example a halogen (F, Cl, Br or I), CN, a $C_1$ to $C_6$ alkyl group, or a $C_1$ to $C_6$ alkoxy group, but is not limited thereto. The halogen may be Cl.

In Chemical Formula 1, the Ph$_1$ and Ph$_2$ may be fused with 1,3-indandione when n is 0 and the Ph$_1$ and Ph$_2$ may be fused with benz[f]indene-1,3-dione when n is 1 and be kink and thus may provide an electron-accepting moiety having a non-linear conjugation structure. This electron accepting moiety may improve absorption intensity without shifting the absorption wavelength position of the compound compared with an electron accepting moiety having a linear conjugation structure. The compound represented by Chemical Formula 1 selectively absorbs light in the green wavelength region, because absorption intensity in a green wavelength region is increased.

In addition, the compound having relatively high absorption intensity may realize a relatively thin active layer having a photo-conversion function in an organic photoelectric device. Since the relatively thin active layer may make a gap between first and second electrodes narrower, a thinner organic photoelectric device may be operated by stronger electric field strength at the same voltage. Herein, an organic photoelectric device having relatively high efficiency may be provided.

In Chemical Formula 1, $R^1$ to $R^6$ may independently be one of hydrogen, a substituted or unsubstituted $C_1$ to $C_{10}$ alkyl group, a substituted or unsubstituted $C_6$ to C12 aryl group, a substituted or unsubstituted $C_4$ to $C_{10}$ heteroaryl group, a halogen, and CN.

$Ar^1$ and $Ar^2$ may independently be a substituted or unsubstituted $C_6$ to $C_{30}$ aryl group or a substituted or unsubstituted $C_4$ to $C_{30}$ heteroaryl group where aromatic rings are present singularly or fused to each other, for example a substituted or unsubstituted $C_6$ to $C_{20}$ aryl group or a C8 to $C_{20}$ aryl group. That is, when a single bond or other linking groups are present between the aromatic rings to link the aromatic rings group, a conjugation structure may be broken and a desirable conjugation length is difficult to obtain.

At least one of $Ar^1$ and $Ar^2$ may be one of a naphthyl group or an anthracenyl group, and in example embodiments a naphthyl group may be desirable. When at least one of $Ar^1$ and $Ar^2$ is a naphthyl group or an anthracenyl group, intermolecular interactions may be decreased, and thus aggregation among molecules in a film state is reduced or prevented. In example embodiments, absorption selectivity in a green wavelength may be improved. When the $Ar^1$ and $Ar^2$ are independently an alkyl group or are fused to each other to provide an N-containing cycloalkyl group, instead of the aromatic group, the compound structure has planarity and thus a full width at half maximum (FWHM) of a light absorption curve may become undesirably wide.

Examples of the compound for an organic photoelectric device may be a compound represented by Chemical Formula 2.

[Chemical Formula 2]

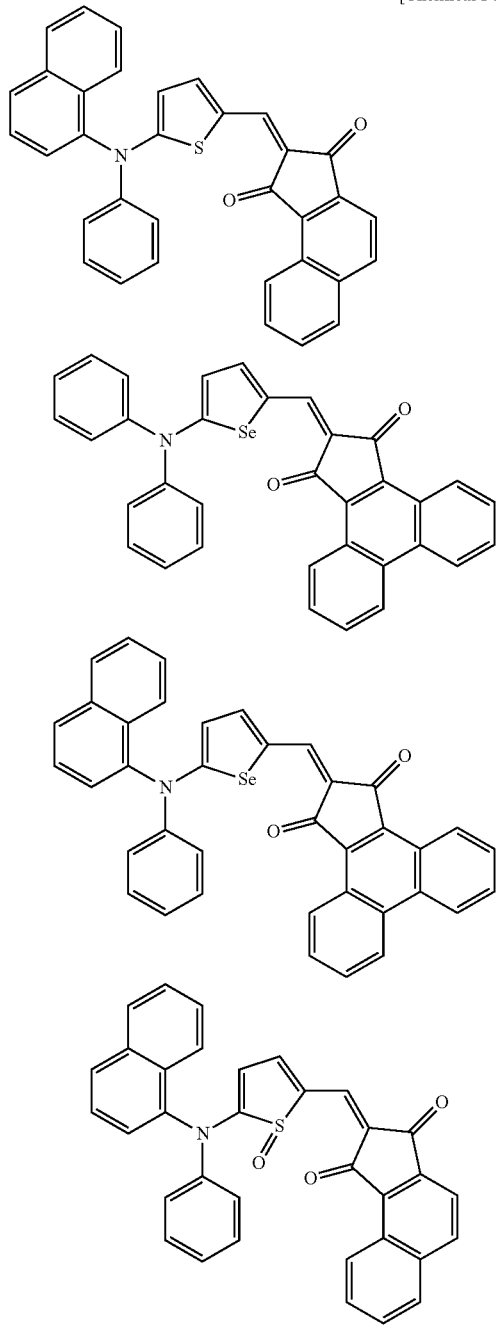

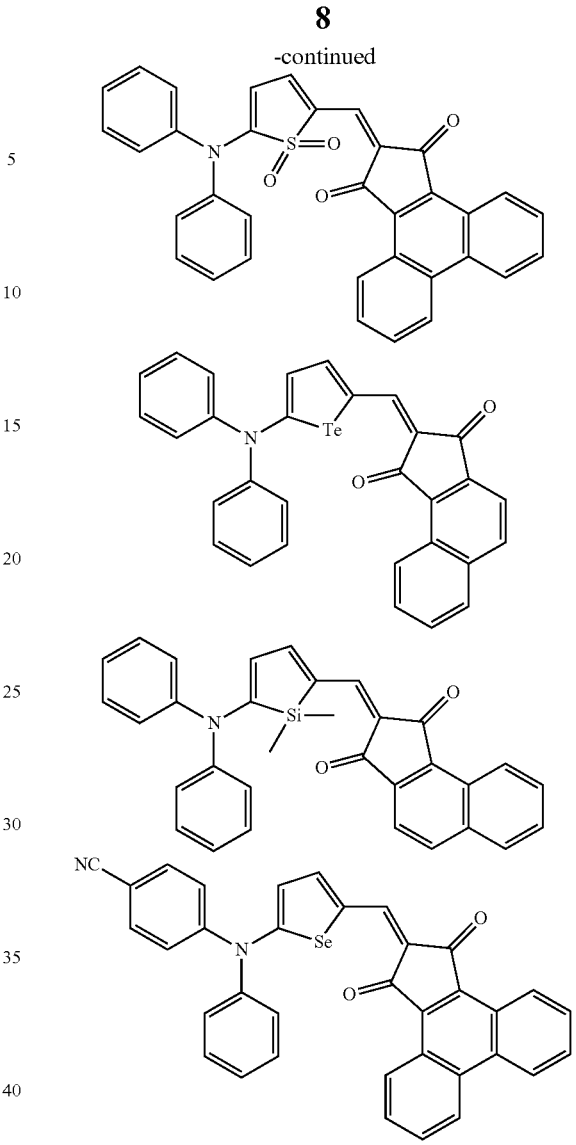

The semiconductor compound is a compound selectively absorbing light in a green wavelength region, and may have a maximum absorption wavelength ($\lambda_{max}$) in a wavelength region of about 500 nm to about 600 nm, for example about 530 nm to about 570 nm, about 530 nm to about 560 nm, or about 530 nm to about 550 nm.

The compound for an organic photoelectric device may exhibit a light absorption curve having a full width at half maximum (FWHM) of about 50 nm to about 120 nm, and specifically about 50 nm to about 110 nm or about 50 nm to about 100 nm, in a thin film state. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

Since the compound for an organic photoelectric device works as a p-type semiconductor, the compound may be appropriately used, as long as it has a higher LUMO level than an n-type semiconductor. For example, when the compound is mixed with an n-type material, e.g., fullerene, the compound desirably has a higher LUMO level than 4.2 eV than the fullerene having a LUMO level of 4.2 eV. As for the appropriate HOMO-LUMO level of the compound, when the compound for an organic photoelectric device has a HOMO level ranging from about 5.0 eV to about 5.8 eV and an energy bandgap ranging from about 1.9 eV to about 2.3 eV, the LUMO level of the compound is in a range of about 3.9 eV to about 2.7 eV. The compound for an organic photoelectric device having a HOMO level, an LUMO level and an energy bandgap within the ranges may be used as a p-type semiconductor compound effectively absorbing light in a green wavelength region, and thus has relatively high external quantum efficiency (EQE) and resultantly improves photoelectric conversion efficiency.

The compound for an organic photoelectric device may have a molecular weight of about 300 to about 1500, more specifically about 350 to about 1200, and even more specifically about 400 to about 900. When the compound has a molecular weight within the range, the compound may be reduced or prevented from being crystallized as well as from being thermally decomposed during formation of a thin film through deposition.

The deposition may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The compound for an organic photoelectric device has, for example, greater than or equal to about 10° C. higher melting point than the deposition temperature and thus may be desirably used for the deposition.

The compound for an organic photoelectric device may be a p-type semiconductor compound.

Hereinafter, an organic photoelectric device including the compound according to example embodiments is described with reference to drawings.

FIG. 1 is a cross-sectional view showing an organic photoelectric device according to example embodiments.

Referring to FIG. 1, an organic photoelectric device 100 according to example embodiments includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor (e.g., indium tin oxide (ITO) or indium zinc oxide (IZO)), or a metal thin layer of a thin single layer or multilayer. When one of the first electrode 10 and the second electrode 20 is a non-light-transmitting electrode, it may be made of, for example, an opaque conductor (e.g., aluminum (Al)).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound for an organic photoelectric device may act as a p-type semiconductor compound in the active layer 30.

The active layer 30 may be formed by depositing the compound for an organic photoelectric device and an n-type semiconductor compound, for example, $C_{60}$ in a volume ratio of about 0.9:1 to about 1.1:1 and specifically, in a volume ratio of about 1:1 and have an absorption coefficient of greater than or equal to about $6 \times 10^4$ cm$^{-1}$, for example, in a range of about $6 \times 10^4$ cm$^{-1}$ to about $6.7 \times 10^4$ cm$^{-1}$. In this way, the active layer 30 having such a relatively high absorption coefficient may be realized to be relatively thin. The relatively thin active layer 30 may make a gap between the first electrode 10 and the second electrode 20 narrower, and thus a thinner organic photoelectric device may be operated by stronger electric field strength at the same voltage. Herein, an organic photoelectric device having relatively high efficiency may be provided.

The active layer 30 may selectively absorb light in a green wavelength region, and the active layer 30 including the compound may have a maximum absorption wavelength ($\lambda_{max}$) at about 500 nm to about 600 nm, for example about 530 nm to about 570 nm, about 530 nm to about 560 nm or about 530 nm to about 550 nm.

The active layer 30 may exhibit a light absorption curve having a relatively narrow full width at half maximum (FWHM) of about 50 nm to about 120 nm, and specifically 50 nm to about 110 nm or about 50 nm to about 100 nm, in a thin film state. Accordingly, the active layer 30 has relatively high selectivity for light in a green wavelength region.

The active layer 30 may further include an n-type semiconductor compound for forming a pn junction.

The n-type semiconductor compound may be one of sub-phthalocyanine, fullerene or a fullerene derivative, thiophene or a thiophene derivative, and a combination thereof. The fullerene or fullerene derivative may be selected from $C_{60}$, a $C_{60}$ derivative, C70, C70 derivative and a combination thereof.

The subphthalocyanine or subphthalocyanine derivative may be represented by Chemical Formula 3.

[Chemical Formula 3]

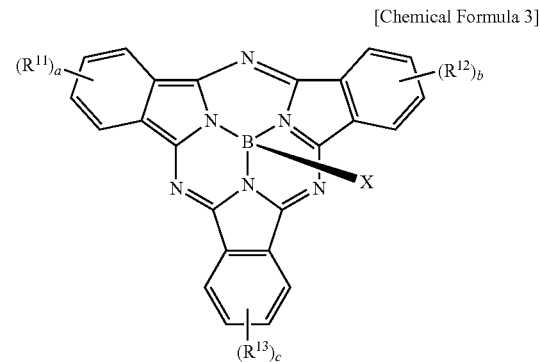

In Chemical Formula 3, $R^{11}$ to $R^{13}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, halogen, a halogen-containing group, and a combination thereof, a, b and c are integers ranging from 1 to 3, and X is a halogen, for example F or Cl.

The halogen refers to F, Cl, Br, or I and the halogen-containing group refers to an alkyl group where at least one of hydrogen is replaced by F, Cl, Br, or I.

The thiophene derivative may be, for example represented by Chemical Formula 4 or 5 but is not limited thereto.

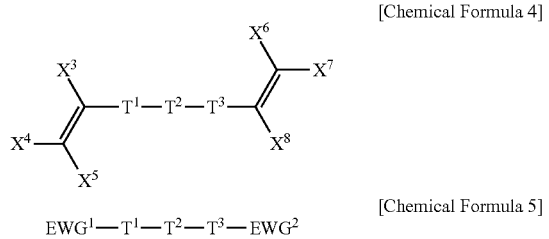

[Chemical Formula 4]

[Chemical Formula 5]

$$EWG^1-T^1-T^2-T^3-EWG^2$$

In Chemical Formulae 4 and 5, $T^1$, $T^2$, and $T^3$ are independently aromatic rings including substituted or unsubstituted thiophene moieties, $T^1$, $T^2$ and $T^3$ are independently present or are fused to each other, $X^3$ to $X^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a cyano group, and a combination thereof, and $EWG^1$ and $EWG^2$ are independently electron withdrawing groups.

For example, in Chemical Formula 4, at least one of $X^3$ to $X^8$ is an electron withdrawing group, for example a cyano group.

The active layer 30 may further include a second p-type semiconductor compound selectively absorbing green light. The p-type semiconductor compound may be a compound represented by Chemical Formula 6.

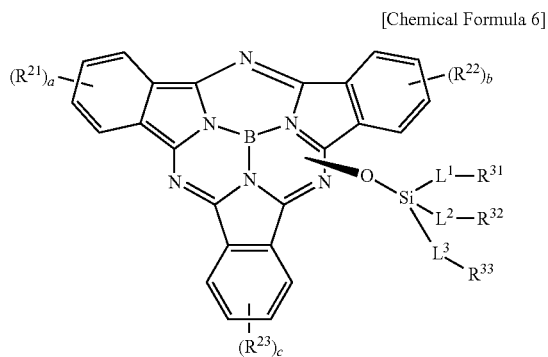

[Chemical Formula 6]

In Chemical Formula 6, $R^{21}$ to $R^{23}$ are independently one of hydrogen, a substituted or unsubstituted $C_1$ to $C_{30}$ aliphatic hydrocarbon group, a substituted or unsubstituted $C_6$ to $C_{30}$ aromatic hydrocarbon group, a substituted or unsubstituted $C_1$ to $C_{30}$ aliphatic heterocyclic group, a substituted or unsubstituted $C_2$ to $C_{30}$ aromatic heterocyclic group, a substituted or unsubstituted $C_1$ to $C_{30}$ alkoxy group, a substituted or unsubstituted $C_1$ to $C_{30}$ aryloxy group, a thiol group, a substituted or unsubstituted $C_1$ to $C_{30}$ alkylthio group, a substituted or unsubstituted $C_6$ to $C_{30}$ arylthio group, a cyano group, a cyano-containing group, a halogen, a halogen-containing group, a substituted or unsubstituted sulfonyl group (e.g., one of a substituted or unsubstituted C0 to $C_{30}$ aminosulfonyl group, a substituted or unsubstituted $C_1$ to $C_{30}$ alkylsulfonyl group, and a substituted or unsubstituted arylsulfonyl group), and a combination thereof, or $R^{21}$ to $R^{23}$ are independently present or are fused to each other to provide a ring, $L^1$ to $L^3$ are independently one of a single bond, a substituted or unsubstituted $C_1$ to $C_{30}$ alkylene group, a substituted or unsubstituted $C_6$ to $C_{30}$ arylene group, a divalent substituted or unsubstituted $C_3$ to $C_{30}$ heterocyclic group, and a combination thereof, $R^{31}$ to $R^{33}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted $C_6$ to $C_{30}$ arylamine group, a substituted or unsubstituted silyl group, and a combination thereof, and a to c are independently integers ranging from 0 to 4.

The second p-type semiconductor compound selectively absorb green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, etc.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm, and specifically, about 5 nm to about 300 nm or about 5 nm to about 200 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the organic photoelectric device 100, when light enters from the first electrode 10 and/or second electrode 20, and when the active layer 30 absorbs light having a given or predetermined wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to example embodiments is described with reference to FIG. 2.

Figure 2:
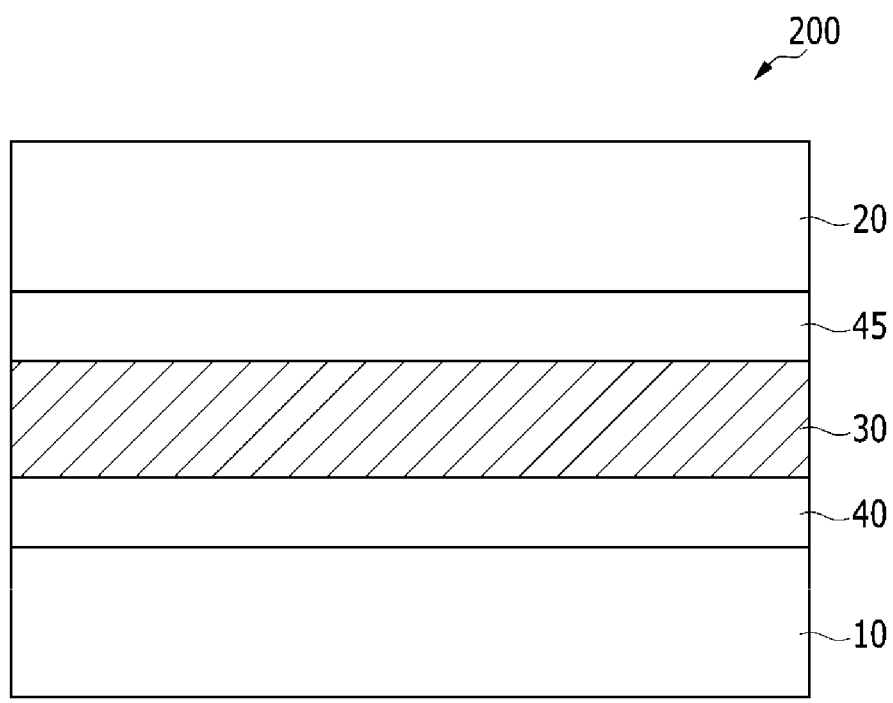
FIG. 2 is a cross-sectional view showing an organic photoelectric device according to example embodiments.

FIG. 2 provides a cross-sectional view showing an organic photoelectric device according to example embodiments.

Referring to FIG. 2, an organic photoelectric device 200 according to example embodiments includes a first electrode 10 and a second electrode 20 facing each other, and an active layer 30 between the first electrode 10 and the second electrode 20, like the example embodiment illustrated in FIG. 1.

However, the organic photoelectric device 200 according to example embodiments further includes charge auxiliary layers 40 and 45 between the first electrode 10 and the active layer 30, and the second electrode 20 and the active layer 30, unlike the example embodiment illustrated in FIG. 1. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for reducing or preventing electron transport, an electron injection layer (EIL) for facilitating electron injection, an electron transport layer (ETL) for facilitating electron transport, and a hole blocking layer (HBL) for reducing or preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide (e.g., molybdenum oxide, tungsten oxide, nickel oxide, etc).

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl ($\alpha$-NPD), m-MTDATA, 4,4',4''-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl ($\alpha$-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
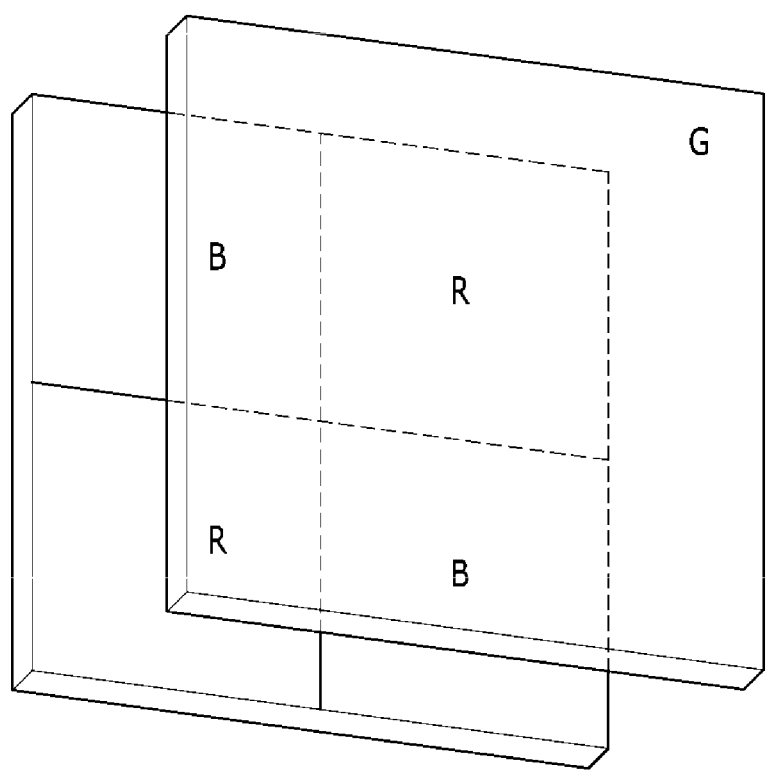
FIG. 3 is a schematic top plan view showing an organic CMOS image sensor according to example embodiments.
Figure 4:
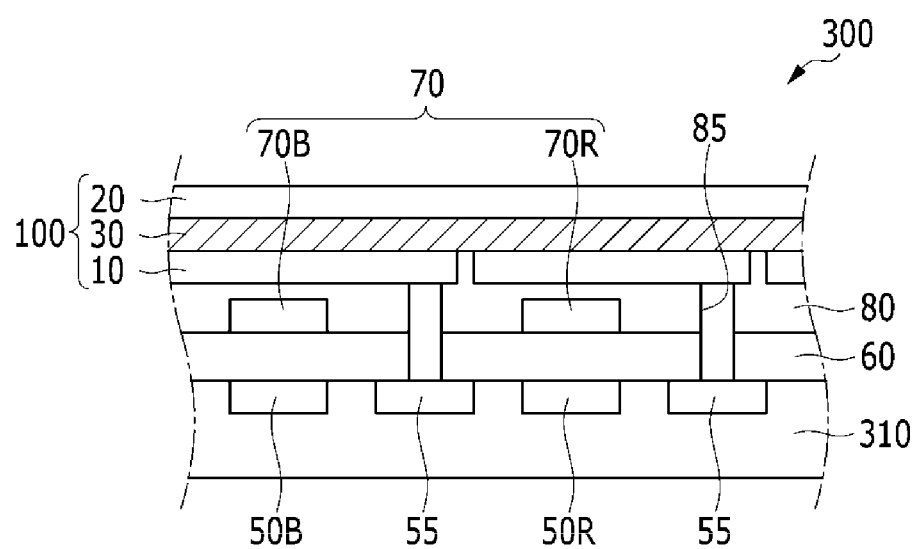
FIG. 4 is a cross-sectional view showing the organic CMOS image sensor of FIG. 3.

FIG. 3 is a schematic top plan view showing an organic CMOS image sensor according to example embodiments, and FIG. 4 is a cross-sectional view of the organic CMOS image sensor of FIG. 3.

Referring to FIGS. 3 and 4, an organic CMOS image sensor 300 according to example embodiments includes a semiconductor substrate 310 integrated with photo-sensing devices 50B and 50R, a transmission transistor (not shown), a charge storage device 55, a lower insulation layer 60, a color filter layer 70, an upper insulation layer 80, and an organic photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage device 55 may be integrated in each pixel, and as shown in the drawing, the photo-sensing devices 50B and 50R may be respectively included in a blue pixel and a red pixel and the charge storage device 55 may be included in a green pixel.

The photo-sensing devices 50B and 50R sense light, the information sensed by the photo-sensing devices may be transferred by the transmission transistor, the charge storage device 55 is electrically connected with the organic photoelectric device 100, and the information of the charge storage device 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material, e.g., a silicon oxide and/or a silicon nitride, or a low dielectric constant (low K) material, e.g., SiC, SiCOH, SiCO, and SiOF. The lower insulation layer 60 has a trench exposing the charge storage device 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In example embodiments, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothes the surface. The upper insulation layer 80 and the lower insulation layer 60 may include a contact hole (not shown) exposing a pad, and a through-hole 85 exposing the charge storage device 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

Figure 5:
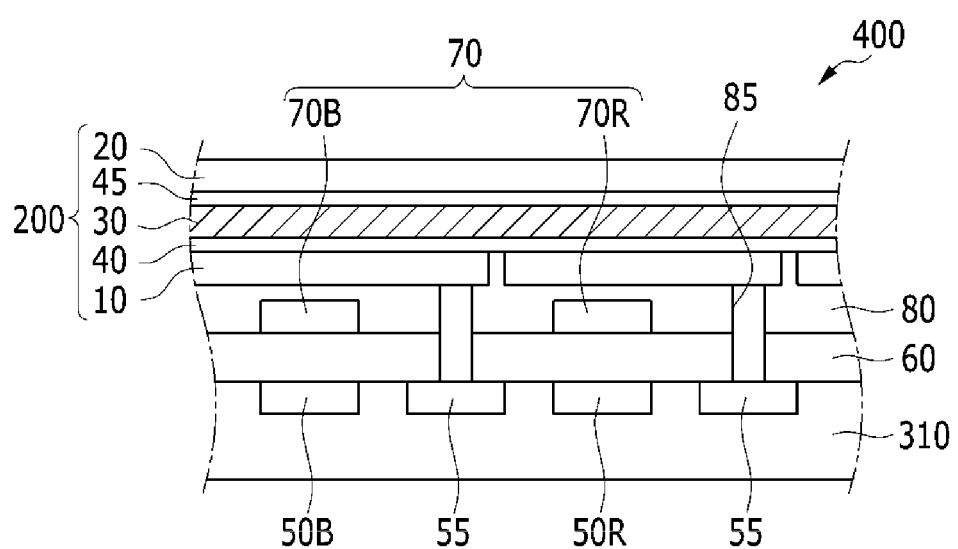
FIG. 5 is a schematic cross-sectional view showing an organic CMOS image sensor according to example embodiments.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
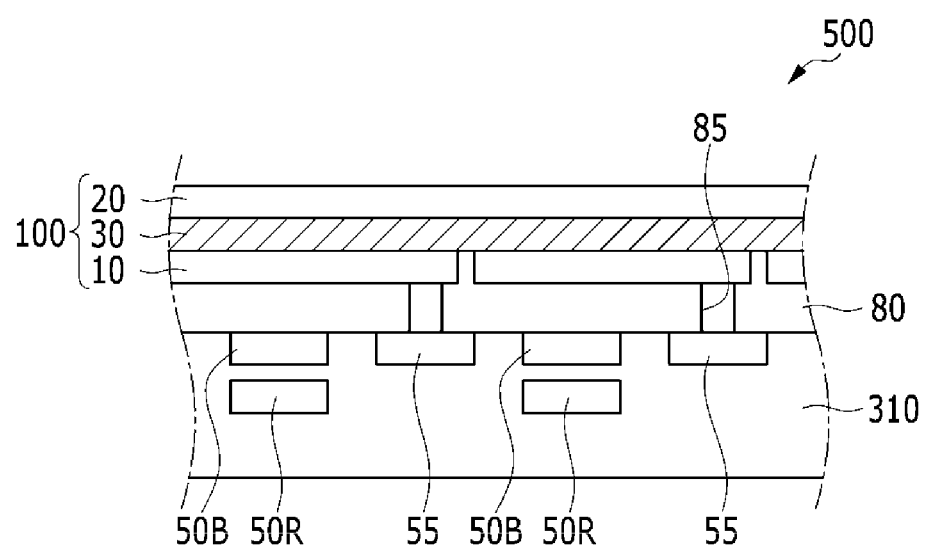
FIG. 6 is a schematic cross-sectional view showing an organic CMOS image sensor according to example embodiments.

FIG. 6 is a cross-sectional view showing the organic CMOS image sensor according to example embodiments.

Referring to FIG. 6, the organic CMOS image sensor 500 includes a semiconductor substrate 310 integrated with photo-sensing devices 50B and 50R, a transmission transistor (not shown), a charge storage device 55, an insulation layer 80, and an organic photoelectric device 100, like the example embodiment illustrated in FIG. 5.

However, the organic CMOS image sensor 500 according to example embodiments illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage device 55, and the information of the charge storage device 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
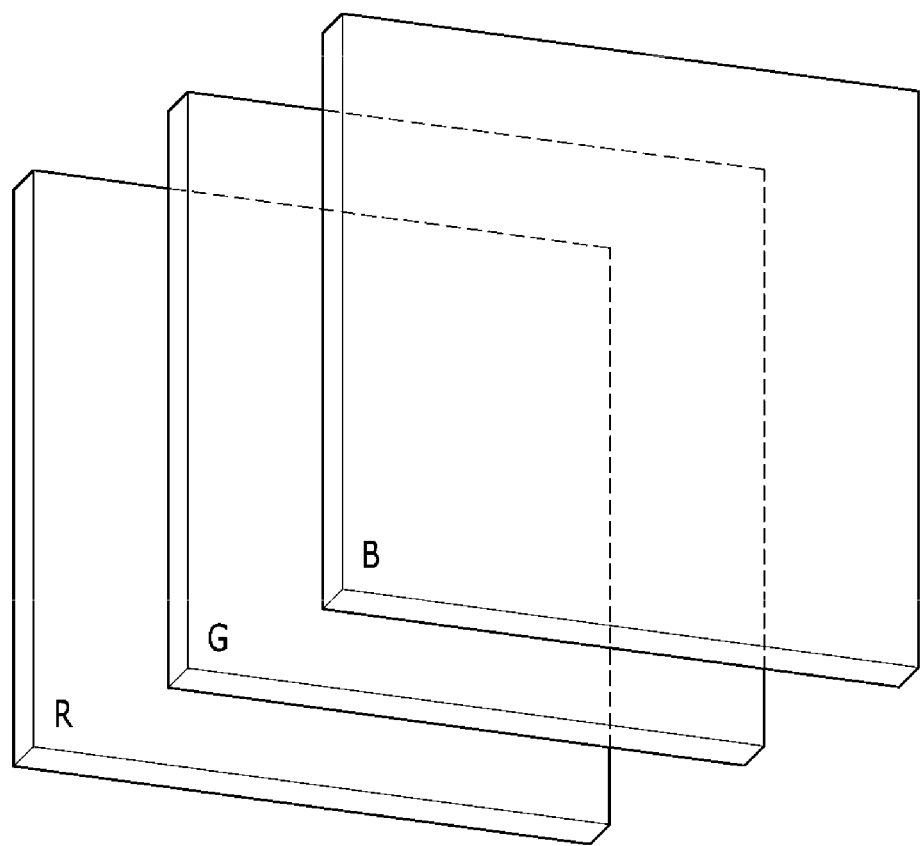
FIG. 7 is a schematic view showing an organic CMOS image sensor according to example embodiments.

FIG. 7 is a schematic view showing an organic CMOS image sensor according to example embodiments.

Referring to FIG. 7, the organic CMOS image sensor according to example embodiments includes a green photoelectric device (G) selectively absorbing light in a green wavelength region, a blue photoelectric device (B) selectively absorbing light in a blue wavelength region, and a red photoelectric device selectively absorbing light in a red wavelength region that are stacked.

In the drawing, the red photoelectric device, the green photoelectric device, and the blue photoelectric device are sequentially stacked, but the stack order may be changed without limitation.

The green photoelectric device may be the above organic photoelectric device 100, the blue photoelectric device may include electrodes facing each other and an active layer interposed therebetween and including an organic material selectively absorbing light in a blue wavelength region, and the red photoelectric device may include electrodes facing each other and an active layer interposed therebetween and including an organic material selectively absorbing light in a red wavelength region.

As described above, the organic photoelectric device selectively absorbing light in a green wavelength region, the organic photoelectric device selectively absorbing light in a red wavelength region, and the organic photoelectric device selectively absorbing light in a blue wavelength region are stacked, and thereby a size of an image sensor may be decreased and a down-sized image sensor may be realized.

The image sensor may be applied to various electronic devices, for example, a mobile phone and/or a digital camera, but is not limited thereto.

Hereinafter, the present disclosure is illustrated in more detail with reference to examples. However, these are examples, and the present disclosure is not limited thereto.

Synthesis Example 1: Synthesis of Compounds Represented by Chemical Formulae 1a and 1

Compounds represented by Chemical Formulae 1a and 1b are synthesized according to a method represented by Reaction Scheme 1.

[Reaction Scheme 1]

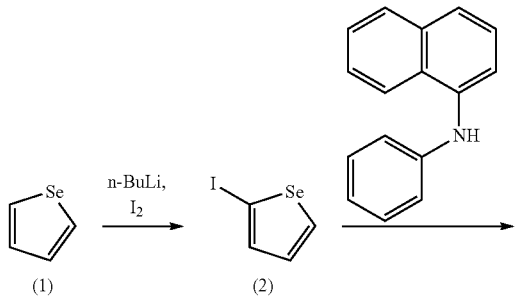

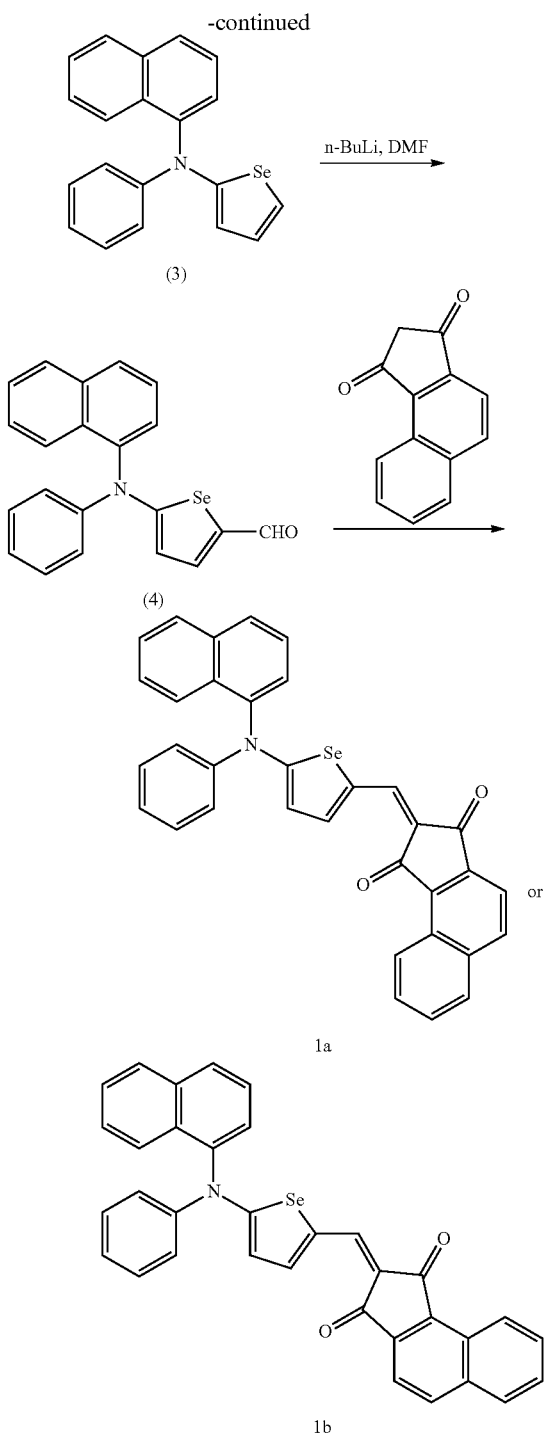

obtaining 2.7 g of naphthylphenylaminoselenophene of a compound (3) (a yield of 65%). Subsequently, 2.0 g (5.7 mmol) of the compound (3) is dissolved in 30 ml of anhydrous THF, and 3.9 ml of a heptane solution of n-BuLi (a concentration: 1.6 M) is slowly added thereto in a dropwise fashion at 0° C. The mixed solution is stirred at 40° C. for 30 minutes and cooled down to −78° C., and 1.0 ml of anhydrous dimethyl formamide (DMF) is added thereto. Subsequently, an ammonium chloride aqueous solution is added to the reaction solution, the mixture is stirred and then, treated with ethylacetate to perform an extraction, and an organic layer therefrom is concentrated under a reduced pressure and purified through silica gel column chromatography, obtaining 1.0 g of a compound (4) (a yield: 47%).

0.5 g (1.3 mmol) of the compound (4) is suspended in ethanol, 0.3 g of 1H-cyclopenta[a]naphthalene-1,3(2H)-dione is added thereto and reacted therewith at 50° C. for 2 hours, obtaining 0.67 g of a mixture of compounds represented by Chemical Formulae 1a and 1b (a mole ratio of 1:1) (a yield of 92%). The mixture of compounds represented by Chemical Formulae 1a and 1 b (a mole ratio of 1:1) is sublimated and purified up to purity of 99.5%.

$^1$H NMR ppm (CDCl3) 9.2 (dd)-1H, 8.2-7.2 (m)-19H, 6.3 (dd)-1H.

Synthesis Example 2: Synthesis of Compounds Represented by Chemical Formulae 1c and 1d A mixture of compounds represented by Chemical Formulae 1c and 1 d (a ratio of 1:1) is obtained (a yield: 95%) according to the same method as Synthesis Example 1 except for changing the naphthylphenylamine into diphenylamine.

$^1$H NMR ppm (CDCl3) 9.22 (d)-1H, 8.13 (d)-1H, 7.88-7.92 (m)-3H, 7.74 (d)-1H, 7.65-7.68 (m)-2H, 7.4-7.5 (m)-8H, 7.30-7.40 (m)-2H. 6.49 (d)-1H

[Chemical Formula 1c]

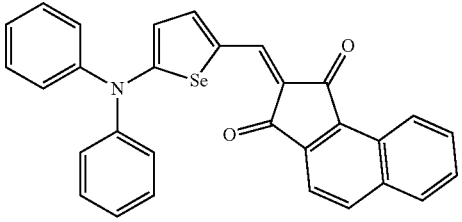

[Chemical Formula 1d]

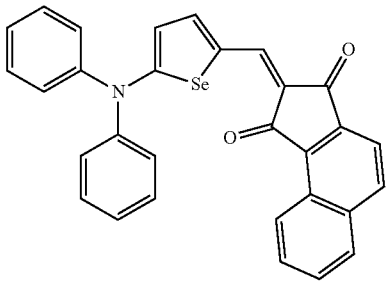

2-iodoselenophene (a compound (2)) is synthesized in a method described in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935. 3.6 g (14.2 mmol) of 2-iodoselenophene and 2.8 g (12.8 mmmol) of 1-naphthylphenylamine is heated and refluxed in 100 ml of anhydrous toluene under presence of 10 mol % of Pd(dba)$_2$, 10 mol % of P(tBu)$_3$, and 1.48 g of NaOtBu for 5 hours.

Subsequently, a product obtained therefrom is separated and purified through silica gel column chromatography, Synthesis Example 3: Synthesis of Compound Represented by Chemical Formula 1e A compound represented by Chemical Formula 1e is obtained (a yield of 95%) according to the same method as Synthesis Example 1 except for using 1H-cyclopenta[l]phenanthrene-1,3(2H)-dione instead of the 1H-cyclopenta[a]naphthalene-1,3(2H)-dione.

¹H NMR (CDCl3), 9.5 (d)-1H, 9.37 (d)-1H, 8.67 (d)-2H, 7.21-8.05 (m)-18H, 6.29 (d)-1H

[Chemical Formula 1e]

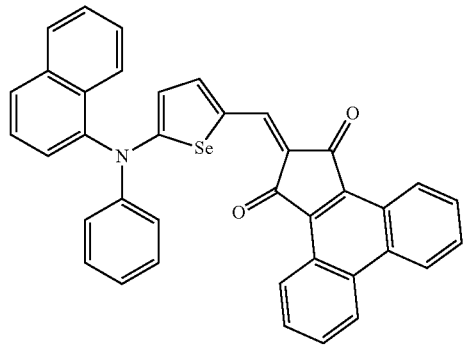

Synthesis Example 4: Synthesis of Compound Represented by Chemical Formula 1f A compound represented by Chemical Formula 1 f is obtained (a yield of 93%) according to the same method as Synthesis Example 1 except for using 1H-cyclopenta[l]phenanthrene-1,3(2H)-dione instead of the 1H-cyclopenta[a]naphthalene-1,3(2H)-dione and 4-(phenylamino)benzonitrile instead of the 1-naphthylphenylamine.

¹H NMR (CDCl3), 8.98 (d)-2H, 8.32 (s)-1H, 8.11 (d)-2H, 7.36-7.68 (m)-11H, 7.14 (s)-1H, 7.00 (d)-2H, 6.59 (d)-1H

[Chemical Formula 1f]

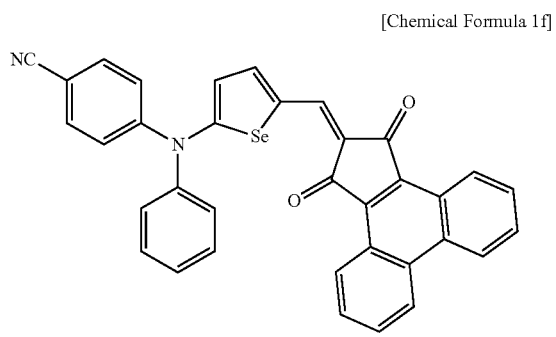 [SMILES: N#Cc1ccc(N(c2ccccc2)c2ccc(C=C3C(=O)c4c(c5ccccc5c5ccccc45)C3=O)[se]2)cc1]

Synthesis Example 5: Synthesis of the Compound Represented by Chemical Formula 1g A compound represented by Chemical Formula 1g is obtained (a yield of 98%) according to the same method as Synthesis Example 1 except for using 1H-cyclopenta[l]phenanthrene-1,3(2H)-dione instead of the 1H-cyclopenta[a]naphthalene-1,3(2H)-dione and 3-(phenylamino)benzonitrile instead of the naphthylphenylamine.

¹H NMR (CDCl3), 8.98 (d)-2H, 8.32 (s)-1H, 8.11 (d)-2H, 7.36-7.68 (m)-11H, 7.14 (s)-1H, 7.00 (d)-2H, 6.59 (d)-1H

[Chemical Formula 1g]

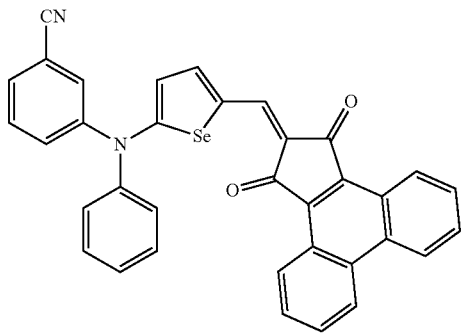

Synthesis Example 6: Synthesis of Compound Represented by Chemical Formula 1h A compound represented by Chemical Formula 1h is obtained (a yield of 98%) according to the same method as Synthesis Example 1 except for using thiophene instead of the selenophene.

¹H NMR (CDCl3), 9.38 (d)-1H, 8.46 (s)-1H, 8.38 (d)-1H, 8.02 (m)-2H, 7.93 (d)-1H, 7.54 (m)-1H, 7.40 (m)-3H, 7.24 (m)-4H, 7.08 (m)-4H, 7.00 (m)-2H, 6.36 (d)-1H

[Chemical Formula 1h]

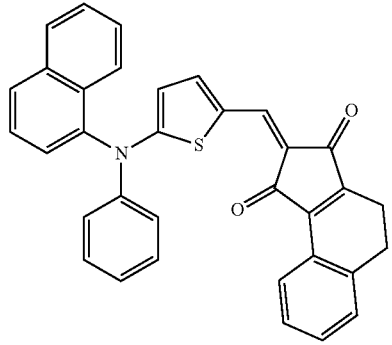

Comparative Synthesis Example 1: Synthesis of Compound Represented by Chemical Formula 1i A compound represented by Chemical Formula 1i is obtained (a yield of 91%) according to the same method as Synthesis Example 1 except for using thiophene instead of the selenophene and 1H-indene-1,3(2H)-dione instead of the 1H-cyclopenta[a]naphthalene-1,3(2H)-dione.

¹H NMR (CDCL3), 8.46 (s)-1H, 8.18 (m)-2H, 7.93 (m)-2H, 7.7-7.5 (m)-8H, 7.40 (d)-1H, 7.24 (m)-2H, 7.04 (m)-2H, 7.04 (m)-2H, 6.36 (d)-1H

[Chemical Formula 1i]

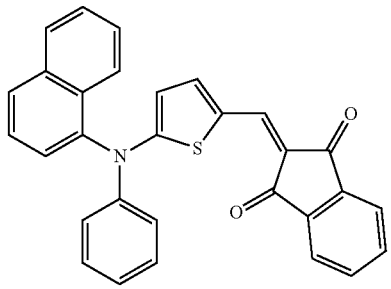

Comparative Synthesis Example 2: Synthesis of Compound Represented by Chemical Formula 1j

A compound represented by Chemical Formula 1j is obtained (a yield of 95%) according to the same method as Synthesis Example 1 except for using 1H-indene-1,3(2H)-dione instead of the 1H-cyclopenta[a]naphthalene-1,3(2H)-dione.

$^1$H NMR (CDCL3), ppm, 8.32 (s)-1H, 8.22 (m)-1H, 8.15 (m)-1H, 7.81 (m)-1H, 7.71 (m)-4H, 7.6-7.3 (m)-7H, 7.14 (s)-1H, 7.00 (dd)-2H, 6.59 (s)-1H

[Chemical Formula 1j]

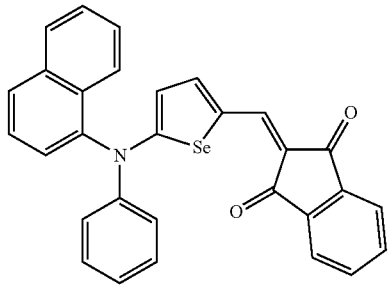

Light Absorption Characteristics of Compounds of Synthesis Examples 1 to 6 and Comparative Synthesis Examples 1 and 2

The light absorption characteristics of the compounds according to Synthesis Examples 1 to 6 and Comparative Synthesis Examples 1 and 2 depending on a wavelength are evaluated. Each compound according to Synthesis Examples 1 to 6 and Comparative Synthesis Examples 1 and 2 (the compound of Synthesis Example 1 is a mixture of the compounds represented by Chemical Formulae 1a and 1b (a mole ratio of 1:1), and the compound of Synthesis Example 2 is a mixture of the compounds represented by Chemical Formulas 1c and 1d (a mole ratio of 1:1) is thermally deposited to form a 70 nm-thick thin film under high vacuum ($<10^{-7}$ Torr) at a rate of 0.5 to 1.0 Å/s, and the maximum absorption wavelength ($\lambda_{max}$) of the thin film is evaluated by radiating an ultraviolet-visible ray (UV-Vis) using Cary 5000 UV spectroscopy (Varian Medical Systems, Inc.).

In addition, each compound according to Synthesis Examples 1 to 6 and Comparative Synthesis Examples 1 and 2 and $C_{60}$ in a volume ratio of 1:1 are codeposited to form a 70 nm-thick thin film, and the absorption coefficient of the thin film is measured by radiating ultraviolet-visible ray (UV-Vis) with Cary 5000 UV spectroscopy (Varian Medical Systems, Inc.).

The absorption coefficient results of the compounds according to Synthesis Examples 1 to 5 and Comparative Synthesis Examples 1 and 2 are provided in Table 1.

TABLE 1

| | Maximum absorption wavelength ($\lambda_{max}$, nm) | Absorption coefficient ($cm^{-1}$) |
|---|---|---|
| Synthesis Example 1 | 536 | 64800 |
| Synthesis Example 2 | 538 | 63000 |
| Synthesis Example 3 | 534 | 62000 |
| Synthesis Example 4 | 530 | 64500 |
| Synthesis Example 5 | 531 | 64200 |
| Comparative Synthesis Example 1 | 522 | 58200 |
| Comparative Synthesis Example 2 | 531 | 58100 |

Referring to Table 1, the compounds according to Synthesis Examples 1 to 5 show a maximum absorption wavelength in a range of 530 nm to 538 nm and an absorption coefficient of greater than or equal to 62000 $cm^{-1}$. On the contrary, the compounds according to Comparative Synthesis Examples 1 and 2 show a maximum absorption wavelength at 522 nm and 533 nm but a lower absorption coefficient than the compounds according to Synthesis Examples 1 to 5. Accordingly, the compounds according to Synthesis Examples 1 to 5 show excellent selective light absorption characteristics about green light and relatively high absorption intensity.

Thermal Stability of Compounds of Synthesis Examples 1 to 6 and Comparative Synthesis Examples 1 and 2

The melting points of the compounds according to Synthesis Examples 1 to 6 and Comparative Synthesis Examples 1 and 2 are measured to evaluate thermal stability. The compounds according to Synthesis Examples 1 and 6 respectively show a melting point at 269° C. and 235° C. In addition, when the compound of Synthesis Example 1 is vacuum-deposited, a temperature in a crucible is 239° C., and when the compound of Synthesis Example 6 is vacuum-deposited, the temperature in the crucible is 234° C. The crucible temperature (deposition temperature) during the vacuum-deposition is a temperature at which the compound starts to be decomposed and measured through a thermal gravimetric analysis (TGA). When the melting point of the compound is lower than the crucible temperature during formation of a thin film through vacuum-deposition, the compound is decomposed and simultaneously, gasified and thus may not form the thin film. Accordingly, the compound should have a higher melting point than a deposition temperature. The compound of Synthesis Example 1 has 30° C. higher melting point than the deposition temperature, and the compound of Synthesis Example 6 melting point has 1° C. higher melting point than the deposition temperature. Accordingly, the compound of Synthesis Example 1 has a large difference between the melting point and the deposition temperature and may secure process stability compared with the compound of Synthesis Example 6.

Example 1: Manufacture of Organic Photoelectric Device

An about 150 nm-thick anode is formed by sputtering ITO on a glass substrate, and an 85 nm-thick active layer is formed by codepositing the compound of Synthesis Example 1 (a mixture of the compounds represented by Chemical Formulae 1a and 1b in a mole ratio of 1:1, a p-type semiconductor compound) and $C_{60}$ (an n-type semiconductor compound) in a volume ratio of 1:1. On the active layer, a molybdenum oxide ($MoO_x$, $0<x≤3$) thin film is deposited to form a 30 nm-thick charge auxiliary layer. Subsequently, a 7 nm-thick cathode is formed by sputtering ITO on the molybdenum oxide thin film, manufacturing an organic photoelectric device.

Examples 2 to 6: Manufacture of Organic Photoelectric Device

Each organic photoelectric device according to Examples 2 to 6 is manufactured according to the same method as Example 1 except for respectively using the compounds of Synthesis Example 2 to 6 instead of the compound of Synthesis Example 1 (the mixture of the compounds represented by Chemical Formulae 1a and 1b in a mole ratio of 1:1). The compound of Synthesis Example 2 uses a mixture of the compounds represented by Chemical Formulae 1c and 1d in a mole ratio of 1:1.

Comparative Examples 1 and 2

Each organic photoelectric device according to Comparative Examples 1 and 2 is manufactured according to the same method as Example 1 except for respectively using the compounds of Comparative Synthesis Examples 1 and 2 instead of the compound of Synthesis Example 1.
External Quantum Efficiency (EQE)

The external quantum efficiency (EQE) of each organic photoelectric device according to Examples 1 to 6 and Comparative Examples 1 and 2 depending on a wavelength and voltage is evaluated.

The external quantum efficiency is measured by using an IPCE measurement system (McScience Inc.). First, a Si photodiode (Hamamatsu Photonics K.K., Japan) is used to calibrate an equipment, the equipment is mounted on the organic photoelectric devices according to Examples 1 to 6, and the external quantum efficiency of the organic photoelectric devices is measured in a wavelength range of about 400 nm to about 800 nm. The external quantum efficiency and the full width at half maximum (FWHM) of the organic photoelectric devices according to Examples 1 to 5 and Comparative Example 2 are measured and provided in Table 2.

TABLE 2

|  | Compound of active layer | EQE (%) (at −3 V) | FWHM (nm) |
| --- | --- | --- | --- |
| Example 1 | Synthesis Example 1 | 50 | 104 |
| Example 2 | Synthesis Example 2 | 54 | 105 |
| Example 3 | Synthesis Example 3 | 51 | 103 |
| Example 4 | Synthesis Example 4 | 53 | 106 |
| Example 5 | Synthesis Example 5 | 52 | 105 |
| Comparative Example 2 | Comparative Synthesis Example 2 | 47 | 100 |

Referring to Table 2, the organic photoelectric devices according to Examples 1 to 5 exhibit an increased full width at half maximum (FWHM) by a small margin compared with the organic photoelectric device of Comparative Example 2, but the organic photoelectric devices according to Examples 1 to 5 exhibit an increased external quantum efficiency by a large margin compared with the organic photoelectric device of Comparative Example 2.

Example 7: Manufacture of Image Sensor

An about 150 nm-thick anode is formed by sputtering ITO on a glass substrate, and a 140 nm-thick active layer is formed by codepositing the compound of Synthesis Example 1 (a mixture of the compounds represented by Chemical Formulae 1a and 1b (a mole ratio of 1:1, a p-type semiconductor compound) and $C_{60}$ (an n-type semiconductor compound) in a thickness ratio of 1.25:1. Subsequently, a molybdenum oxide ($MoO_x$, $0<x≤3$) thin film is deposited to form a 30 nm-thick charge auxiliary layer on the active layer. Then, a 7 nm-thick cathode is formed on the molybdenum oxide thin film by sputtering ITO, manufacturing an organic photoelectric device.

The organic photoelectric device instead of the organic photoelectric device 100 having the structure for an image sensor 300 shown in FIG. 4 is used to manufacture an image sensor.

Examples 8 to 13: Manufacture of Image Sensor

Each organic photoelectric device according to organic photoelectric device is manufactured according to the same method as Example 1 except for respectively using the compounds of Synthesis Examples 2 to 6 instead of the compound of Synthesis Example 1 (the mixture of the compounds represented by Chemical Formulae 1a and 1b in a mole ratio of 1:1) and forming each active layer having a thickness provided in Table 3.
Color Reproducibility (ΔE*ab)

A color difference ΔE*ab between SNR10 when an 18% gray patch in a Macbeth chart is photographed under a light of D-65 and 24 colors in the Macbeth chart.

Herein, lens having an F value of 2.8 and transmittance of 80% are used, and as for an infrared ray-cut filter, general interference lens are used. An image sensor is set to have a pixel size of 1.4 μm and a frame rate of 15 fps.

The SNR10 is obtained in a method provided in "Image Sensors and Image Quality in Mobile Phones" by Juha Alakarhu in the summary of 2007's International Image Sensor Workshop (Ogunquit Me., USA). The SNR10 obtained under ΔE*ab=3 by calibrating a color with CCM (Color Correction Matrix) is provided in Table 3.

TABLE 3

|  | Compound of active layer | Thickness of active layer (nm) | Optimized EQE (%) (at −3 V) | ΔE * ab | SNR10 (lux) |
| --- | --- | --- | --- | --- | --- |
| Example 7 | Synthesis Example 1 | 140 | 67 | 3.0 | 95 |
| Example 8 | Synthesis Example 2 | 145 | 70 | 3.0 | 85 |
| Example 9 | Synthesis Example 3 | 140 | 68 | 3.0 | 93 |
| Example 10 | Synthesis Example 4 | 135 | 68 | 3.0 | 90 |
| Example 11 | Synthesis Example 5 | 135 | 67 | 3.0 | 94 |

Referring to Table 3, the image sensors according to Examples 7 to 11 have SNR10 of 85 to 95 under ΔE*ab=3 by calibrating a color with CCM (Color Correction Matrix) and exhibit relatively high sensitivity at a relatively high-definition pixel of 1.4 μm.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound for an organic photoelectric device represented by Chemical Formula 1:

[Chemical Formula 1]

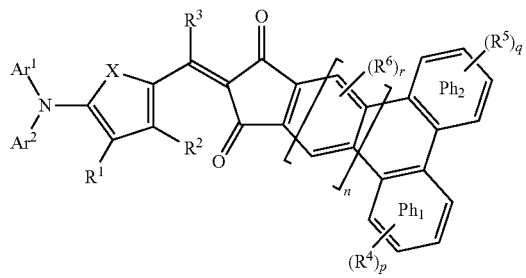

wherein, in Chemical Formula 1,
each of $Ar^1$ and $Ar^2$ are independently one of a substituted or unsubstituted $C_6$ to $C_{30}$ aryl group and a substituted or unsubstituted $C_4$ to $C_{30}$ heteroaryl group,
X is one of Se, Te, S(=O), S(=O)$_2$, and $SiR^aR^b$ (wherein each of $R^a$ and $R^b$ are independently one of hydrogen, a $C_1$ to $C_{10}$ alkyl group, a $C_6$ to $C_{10}$ aryl group, and a $C_5$ to $C_{10}$ heteroaryl group),
each of $R^1$ to $R^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, and CN,
each of p and q are independently integers of 0 to 4,
r is an integer of 0 to 2,
n is 0 or 1, and
each of $Ph_1$ and $Ph_2$ are independently a fused phenylene ring, provided that at least one of $Ph_1$ and $Ph_2$ are present.

2. The compound of claim 1, wherein at least one of $Ar^1$ and $Ar^2$ is one of a naphthyl group and an anthracenyl group.

3. The compound of claim 1, wherein the compound has a maximum absorption wavelength ($\lambda_{max}$) of about 500 nm to about 600 nm.

4. The compound of claim 1, wherein the compound has a maximum absorption wavelength ($\lambda_{max}$) of about 530 nm to about 570 nm.

5. The compound of claim 1, wherein the compound exhibits a light absorption curve having a full width at half maximum (FWHM) in a thin film state of about 50 nm to about 120 nm.

6. The compound of claim 1, wherein the compound is a p-type semiconductor compound.

7. The compound of claim 6, wherein the compound exhibits a light absorption curve having a full width at half maximum (FWHM) in a thin film state of about 50 nm to about 110 nm.

8. An organic photoelectric device comprising
a first electrode and a second electrode facing each other, and
an active layer between the first electrode and the second electrode, the active layer including a compound represented by Chemical Formula 1:

[Chemical Formula 1]

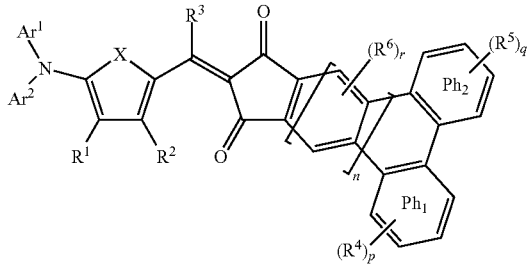

wherein in Chemical Formula 1,
each of $Ar^1$ and $Ar^2$ are independently one of a substituted or unsubstituted $C_6$ to $C_{30}$ aryl group and a substituted or unsubstituted $C_4$ to $C_{30}$ heteroaryl group,
X is one of Se, Te, S(=O), S(=O)$_2$, and $SiR^aR^b$ (wherein each of $R^a$ and $R^b$ are independently one of hydrogen, a $C_1$ to $C_{10}$ alkyl group, a $C_6$ to $C_{10}$ aryl group, and a $C_5$ to $C_{10}$ heteroaryl group),
each of $R^1$ to $R^6$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_4$ to $C_{30}$ heteroaryl group, a halogen, and CN,
each of p and q are independently integers of 0 to 4,
r is an integer of 0 to 2,
n is 0 or 1, and
each of $Ph_1$ and $Ph_2$ are independently a fused phenylene ring, provided that at least one of $Ph_1$ and $Ph_2$ are present.

9. The organic photoelectric device of claim 8, wherein the active layer has an absorption coefficient of greater than or equal to about $6 \times 10^4$ cm$^{-1}$ when including the compound and $C_{60}$ in a volume ratio of about 0.9:1 to about 1.1:1.

10. The organic photoelectric device of claim 8, wherein the active layer has an absorption coefficient of about $6 \times 10^4$ cm$^{-1}$ to about $6.7 \times 10^4$ cm$^{-1}$ when including the compound and $C_{60}$ in a volume ratio of about 0.9:1 to about 1.1:1.

11. The organic photoelectric device of claim 8, wherein the active layer has a maximum absorption wavelength ($\lambda_{max}$) of about 500 nm to about 600 nm.

12. The organic photoelectric device of claim 8, wherein the active layer has a maximum absorption wavelength ($\lambda_{max}$) of about 530 nm to about 570 nm.

13. The organic photoelectric device of claim 8, wherein the active layer exhibits a light absorption curve having a full width at half maximum (FWHM) in a thin film state of about 50 nm to about 120 nm.

14. The organic photoelectric device of claim 8, wherein the active layer exhibits a light absorption curve having a full width at half maximum (FWHM) in a thin film state of about 50 nm to about 110 nm.

15. The organic photoelectric device of claim 8, wherein the compound is a p-type semiconductor compound.

16. The organic photoelectric device of claim 15, wherein the active layer further comprises an n-type semiconductor compound.

17. The organic photoelectric device of claim 16, wherein the n-type semiconductor compound includes one of subphthalocyanine, fullerene or a fullerene derivative, thiophene or a thiophene derivative, and a combination thereof.

18. An image sensor including the organic photoelectric device of claim 8.

19. The image sensor of claim 18, further comprising:
a semiconductor substrate integrated with a plurality of first photo-sensing devices configured to sense light in a blue wavelength region and a plurality of second photo-sensing devices configured to sense light in a red wavelength region, wherein the organic photoelectric device is on the semiconductor substrate and is configured to selectively absorb light in a green wavelength region.

20. The image sensor of claim 19, wherein the plurality of first photo-sensing devices and the plurality of second photo-sensing devices are stacked in a vertical direction on the semiconductor substrate.

21. The image sensor of claim 19, further comprising:
a color filter layer between the semiconductor substrate and the organic photoelectric device, the color filter layer including a blue filter configured to selectively absorb light in a blue wavelength region and a red filter configured to selectively absorb light in a red wavelength region.

22. The image sensor of claim 18, wherein
the organic photoelectric device is a green photoelectric device, and
the green photoelectric device, a blue photoelectric device configured to selectively absorb light in a blue wavelength region, and a red photoelectric device configured to selectively absorb light in a red wavelength region are stacked.

23. An electronic device comprising the image sensor of claim 18.

* * * * *